United States Patent [19]

Kinoshita et al.

[11] Patent Number: 5,753,395
[45] Date of Patent: May 19, 1998

[54] ELECTROPHOTOGRAPHIC PHOTORECEPTOR

[75] Inventors: Akira Kinoshita; Naohiro Hirose; Kazumasa Watanabe; Akihiko Itami, all of Hino, Japan

[73] Assignee: Konica Corporation, Japan

[21] Appl. No.: 614,103

[22] Filed: Mar. 12, 1996

Related U.S. Application Data

[63] Continuation of Ser. No. 861,335, Mar. 30, 1992, abandoned, which is a continuation of Ser. No. 542,726, Jun. 22, 1990, abandoned.

[30] Foreign Application Priority Data

Jun. 30, 1989 [JP] Japan ................................. 1-170360

[51] Int. Cl.$^6$ ................................................ G03G 5/06
[52] U.S. Cl. ............................ 430/78; 430/58; 540/141
[58] Field of Search .......................... 540/141; 430/58, 430/78

[56] References Cited

U.S. PATENT DOCUMENTS 4,701,396 10/1987 Hung et al. ............................ 430/78
4,898,799 2/1990 Fujimaki et al. ...................... 430/78
5,189,155 2/1993 Mayo et al. ........................... 430/78
5,189,156 2/1993 Mayo et al. ........................... 430/78
5,225,551 7/1993 Duff et al. ............................. 430/78

FOREIGN PATENT DOCUMENTS 180930 5/1986 European Pat. Off. .
314100 5/1989 European Pat. Off. .

OTHER PUBLICATIONS

Patent Abstracts of Japan vol. 12 No. 366 (p. 765) (3213) Sep. 30, 1988 JPA–63–116158; May 20, 1988.

Patent Abstracts of Japan vol. 13 No. 11 (C–558) (3359) Jan. 11, 1989 JPA–63–218768; Sep. 12, 1988.

*Primary Examiner*—Christopher D. Rodee
*Attorney, Agent, or Firm*—Jordan B. Bierman; Bierman, Muserlian and Lucas

[57] ABSTRACT

There is disclosed an electrophotographic photoreceptor which comprises a titanylphthalocyanine containing 0.2% by weight or less of chlorine in a crystal form with the X-ray diffraction spectrum to Cu—Kα line having peaks at Bragg's angles 2θ of 9.5°±0.2°, 24.1°±0.2° and 27.2°±0.2°.

7 Claims, 4 Drawing Sheets

ELECTROPHOTOGRAPHIC PHOTORECEPTOR

This application is a Continuation of U.S. patent application Ser. No. 07/861,335, filed Mar. 30, 1992, abandoned, which is a Continuation of U.S. patent application Ser. No. 07/542,726, filed on Jun. 22, 1990, now abandoned.

BACKGROUND OF THE INVENTION

This invention relates to an electrophotographic photoreceptor, particularly to an electrophotographic photoreceptor exhibiting high sensitivity to semiconductor laser beam and LED which can be effectively used for printer, copying machine, etc.

As electrophotographic photoreceptors, there have been widely used inorganic photoreceptors for long time, having photosensitive layers composed mainly of inorganic photoconductive substances such as selenium, zinc oxide and cadmium sulfide, but such inorganic photoreceptors involved various problems. For example, selenium is liable to be deteriorated in characteristics because of crystallization due to heat or contamination with fingerprint, cadmium sulfide is inferior in humidity resistance, durability, and also zinc oxide is inferior in durability. Accordingly, organic photoconductive substances having various advantages are becoming utilized widely as electrophotographic photoreceptors in recent years. Among them, phthalocyanine compounds have high quantum efficiency of photoelectric conversion, and also exhibit high spectral sensitivity even to near-infrared region, and therefore they have attracted attention for electrophotographic photoreceptor adapted particularly for semiconductor laser beam source.

For such purpose, electrophotographic photoreceptors by use of copper phthalocyanine, metal-free phthalocyanine, chloroindium phthalocyanine, chlorogallium phthalocyanine have been reported, but in recent years, particularly titanylphthalocyanine is attracting attention, and a large number of techniques of electrophotographic photoreceptors by use of titanylphthalocyanine have been disclosed as in Japanese Provisional Patent Publications No. 239248/1986, No. 670943/1987, No. 272272/1987 and No. 116158/1988.

Generally speaking, phthalocyanine compounds are prepared by reacting phthlodinitrile, 1,3-diiminoisoindoline, etc. with metal compounds, but in preparation of titanylphthalocyanine for electrophotographic photoreceptor, titanium tetrachloride has been exclusively used as the starting material for the point of reactivity. For example, in preparation of vanadylphthalocyanine having similar structure to titanylphthalocyanine, vanadyl chloride, vanadylacetylacetonate may be available as the starting material, but in preparation of titanylphthalocyanine, if titanylacetylacetonate is used as the starting material, the yield will be markedly lowered, and also purity lowered. For this reason, as the methods for preparation of titanylphthalocyanine for electrophotographic photoreceptor, in addition to Japanese Provisional Patent Publications No. 239248/1986, No. 670943/1987, No. 272272/1987 and No. 116158/1988, they are also disclosed in Japanese Provisional Patent Publications No. 171771/1986, No. 109056/1986, No. 166956/1984, No. 256868/1987, No. 256866/1987, No. 256867/1987, No. 80263/1988, No. 286059/1987, No. 366/1988, No. 37163/1988 and No. 134651/1987, and in all of these cases, the methods by use of titanium tetrachloride have been employed.

When the titanium compounds as mentioned above is used as the starting material, chlorination reaction of phthalocyanine nucleus is accompanied. Since high temperature conditions of 180° C. or higher are required in the conventional preparation method, they are also causes for accelerating the side reaction of chlorination. For this reason, a considerable amount of titanylphthalocyanine chloride cannot be contained in the titanylphthalocyanine of the prior art, and also titanylphthalocyanine chloride once mixed, because it is similar in physical and chemical characteristics to unsubstituted titanylphthalocyanine, cannot substantially be removed by recrystallization. Also, even by sublimation purification, although the ratio of titanylphthalocyanine chloride may be slightly reduced, there are involved such problems that the cost of purification is high, that it is difficult to remove chlorine completely, etc. Therefore, in the prior art, the titanylphthalocyanine which has been employed for electrophotographic photoreceptor contained chlorine compounds. For example, measured values of chlorine contents in preparation examples of titanylphthalocyanine disclosed in the Provisional Patent Publications as mentioned above are as shown in Table 1.

TABLE 1

| Japanese Provisional Patent Publication No. | | Elemental analysis value of Cl (wt %) | Mass spectrum |
|---|---|---|---|
| 109056/1986 | Compound 1 | 0.49 | — |
|  | Compound 2 | 0.5 | — |
|  | Compound 3 | 5 | — |
| 171771/1986 | Example 1 | 0.87 | — |
|  | Example 2 | 0.92 | — |
|  | Example 3 | 0.87 | — |
| 67094/1987 | Preparation example 1 | 0.49 | — |
|  | Preparation example 4 | 0.85 | — |
| 256865/1987 | Example 1 | 0.43 | — |
| 256866/1987 | Example 1 | 0.38 | — |
| 256867/1987 | Example 1 | 0.60 | — |
| 80263/1987 | Preparation example 1 | 0.43 | — |
|  | Preparation example 2 | 0.60 | — |
|  | Preparation example 3 | 0.58 | — |
| 366/1988 | Example 1 | 0.58 | — |
| 37163/1988 | A type preparation example | 0.43 | — |
|  | B type preparation example | 0.60 | — |
| 217050/1987 | Preparation example | — | Including $M^+ = 610$ |
| 239248/1987 | Preparation example | — | Including $M^+ = 610$ |

(Note) $M^+ = 610$ corresponds to chlorinated titanylphthalocyanine

Thus, in the titanylphthalocyanine of the prior art, it has been inevitable to contain about 0.4% by weight of chlorine. The value of 0.4% by weight as chlorine atom corresponds to the content of 7.0% by weight (6.6 mole %) as calculated on titanylphthalocyanine monochloride concentration, which is a very high value as the impurity concentration.

On the other hand, electrophotographic characteristics of phthalocyanine compounds differ remarkably depending on the crystal state thereof, and also it has been known in titanylphthalocyanine that excellent characteristics can be obtained when it has a specific crystal form. Thus, in electrophotographic materials having structure sensitive properties, presence of an impurity introduces structurally defective sites, which will cause damaging of excellent electrophotographic characteristics possessed by a specific crystal form.

Concerning such point, we have investigated intensively in order to obtain titanylphthalocyanine of high purity, and consequently successfully applied a preparation method accompanied with no chlorination reaction, and could prepare an excellent electrophotographic photoreceptor by making the titanylphthalocyanine with little chlorine content thus obtained to have a specific crystal structure.

SUMMARY OF THE INVENTION

An object of the present invention is to provide an electrophotographic photoreceptor which is of high purity and small in residual potential, also stable in potential characteristics even in repeated uses, particularly excellent in potential retaining ability, and stable in charging potential.

Another object of the present invention is to provide an electrophotographic photoreceptor having sufficient sensitivity even to a long wavelength light source such as semiconductor laser, etc.

The above objects of the present invention can be accomplished by incorporating a titanylphthalocyanine containing 0.2% by weight or less, preferably 0.1% by weight or less, of chlorine in a crystal form with the X-ray diffraction spectrum to Cu—Kα line exhibiting peaks at Bragg's angles 2θ of 9.5°±0.2°, 24.1°±0.2°, 27.2°±0.2° in the photosensitive layer.

DESCRIPTION OF THE PREFERRED EMBODIMENTS

The X-ray diffraction spectrum is measured under the following conditions, and the above-mentioned peak refers to the projected portion of sharp angle differing distinctly from noise.

| X-ray tube | Cu |
|---|---|
| Voltage | 40.0 KV |
| Current | 100 mA |
| Start angle | 6.0 deg. |
| Stop angle | 35.0 deg. |
| Step angle | 0.02 deg. |
| Measurement time | 0.50 sec. |

The chlorine content can be also determined by conventional elemental analysis measurement, but it can be also determined by elemental analysis by use of a chlorine-sulfur analyzer "TSX-10" manufactured by Mitsubishi Kasei Corp.

The more desirable chlorine content in the present invention is 0.08% or less, most desirably detection limit or less in these measurement methods.

As the method for obtaining titanylphthalocyanine with little chlorine content, it is conceivable to subject the titanylphthalocyanine obtained by use of conventional titanium tetrachloride to sublimation purification. However, this method is poor in efficiency and high in cost, and it is difficult to remove chlorine completely. Accordingly, it is preferable to prepare it directly at high purity by using a titanium compound represented by the formula (I) shown below without accompaniment of chlorination.

wherein $X_1$, $X_2$, $X_3$, $X_4$ each represent, $—OR_1$, $—SR_2$,

Here, $R_1$ to $R_5$ each represent hydrogen atom, an alkyl group, an alkenyl group, an aryl group, an aralkyl group, an acyl group, an aryloyl group, a heterocyclic group, and these groups may also have any desired substituent. $X_1$ to $X_4$ may be also bonded in any desired combination to form a ring.

Y represents a ligand, and n represents 0, 1 or 2. Among them, those wherein $X_1$ to $X_4$ are each $—OR_1$ can be mentioned as desirable ones for such points as reactivity, handle-ability, cost, etc.

As the preparation method, various reaction systems may be possible, but as the representative method, the method shown by the following reaction scheme may be employed.

In the scheme, $R_6$ to $R_{21}$ each represent a hydrogen atom or a substituent. The substituent may be optinal including, for example, an alkyl group, an alkoxy group, an alkoxythio group, an aryl group, an aryloxy group, an arylthio group, an acyl group, a carbamoyl group, a sulfamoyl group, an amino group, an alkylamino group, an arylamino group, a halogen atom, a nitro group and a cyano group.

In such preparation method in the present invention, since no attack of active chlorine is received, chlorination of phthalocyanine nucleus can be completely avoided. Also, as compared with the method by use of titanium tetrachloride of the prior art, the reactivity is higher and the reaction can be permitted to proceed under more mild environment, which is not only advantageous for preparation conditions but can also inhibit side reactions to suppress the impurities at minimum.

Specific examples of useful titanium compounds are shown below.

(1) $(C_4H_9O)_4Ti$ (2) $(i\text{-}C_3H_7O)_4Ti$

(3) $(C_2H_5O)_4Ti$

(4) $(i\text{-}C_4H_9O)_4Ti$

(5) $(C_{18}H_{37}O)_4Ti$

(6) $(C_3H_7O)_4Ti$

(7) $(i\text{-}C_3H_7O)_2Ti(CH_3COCHCOCH_3)_2$ (8)

(9)

(10)

(11)

(12)

(13)

(14)

(15)

(16)

(17)

(18)

(19)

As the solvent for the reaction, various solvents can be used. For example, there may be included aliphatic solvents such as dioxane, cyclohexane, sulforane, dimethyl sulfoxide, dimethylformamide, dimethylacetamide and methylpentanone; aromatic solvents such as chlorobenzene, dichlorobenzene, bromobenzene, nitrobenzene, chloronaphthalene, tetralin, pyridine and quinoline, as representative ones, but for obtaining a product of high purity, it is desirable to use one having solubility to some extent for titanylphthalocyanine.

The reaction temperature, which may differ depending on the titanium coupling agent, is approximately 100° to 180° C. Also, in this respect, as compared with the reaction of the prior art which required high temperature of 180° to 240° C., the present invention is advantageous from the standpoint of prevention of side reactions.

The titanylphthalocyanine of high purity thus obtained can be treated with an appropriate solvent to give a desired crystal form. As the device to be used for the treatment, in addition to general stirring devices, homomixer, disperser, agitator, or ball mill, sand mill and attritor can be included.

In the electrophotographic photoreceptor of the present invention, the above-described titanylphthalocyanine may be used as the carrier generating substance, but otherwise, another carrier generating substance may be also used in combination. As such carrier generating substance, in the first place a titanylphthalocyanine different in crystal form from the present invention, and also other phthalocyanines pigments, azo pigments, anthraquinone pigments, perylene pigments, polycyclic quinone pigments and squarium pigments may be included.

As the carrier transporting substance in the photoreceptor of the present invention, various substances can be employed, but representative are, for example, compounds having nitrogen containing heterocyclic nucleus and fused ring nucleus thereof as represented by oxazole, oxadiazole, thiazole, thiadiazole and imidazole, polyarylalkane type compounds, pyrazoline type compounds, hydrazone type compounds, triarylamine type compounds, styryl type compounds, styryltripheylamine type compounds, β-phenylstyryltriphenylamine type compounds, butadiene type compounds, hexatriene type compounds, carbazole type compounds and fused polycyclic compounds. Specific examples of these carrier transporting substances may include those as disclosed in Japanese Provisional Patent Publication No. 107356/1986, and the structures of particularly representative ones are shown below.

T-1

-continued

T-2

T-3

T-4

T-5

T-6

T-7

T-8

T-9

T-10

T-11

T-12

T-13

T-14

T-15

-continued

T-16

T-17

T-18

T-19

T-20

Figure 1:
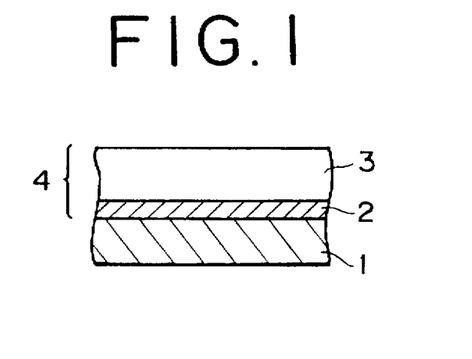
FIGS. 1 through 6 are respective sectional views showing specific examples of layer constitutions of the photoreceptor of the present invention.
Figure 2:
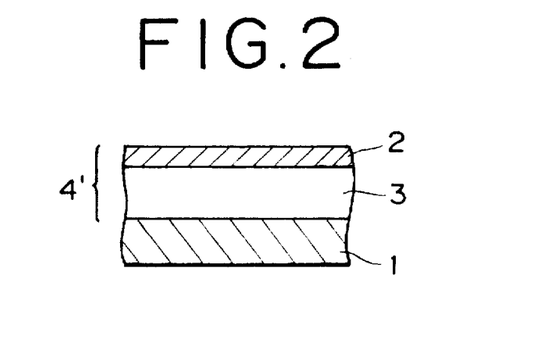
Figure 3:
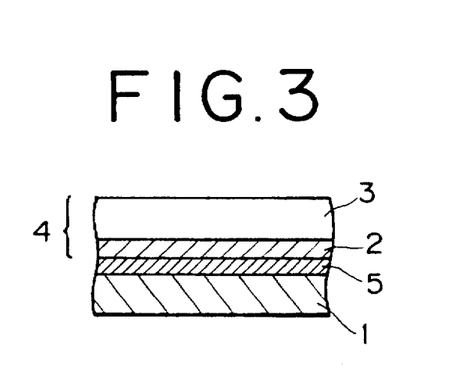
Figure 4:
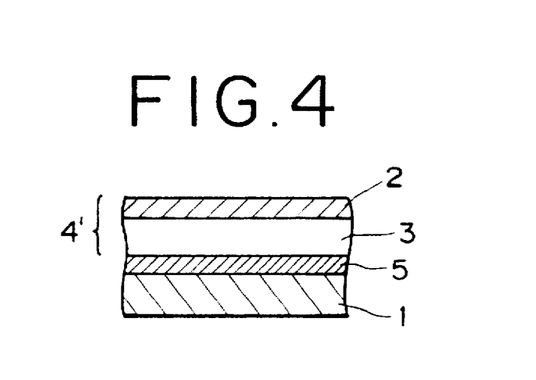
Figure 5:
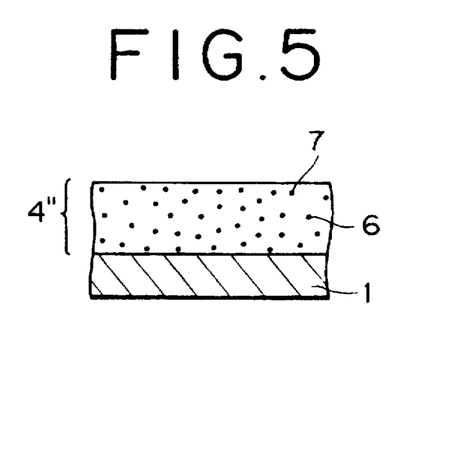
Figure 6:
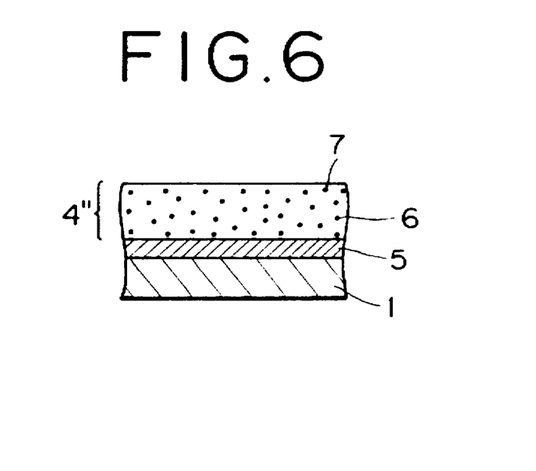

Various forms of constitutions of photoreceptors have been known. The photoreceptor of the present invention can take any form of them, but it should be desirably made a function separation type photoreceptor of the lamination type or the dispersion type. In this case, the constitution becomes generally as shown in FIG. 1 to FIG. 6. The layer constitution shown in FIG. 1 has a carrier generation layer 2 formed on an electroconductive support 1, and a carrier transporting layer 3 laminated thereon to form a photosensitive layer 4, and FIG. 2 has a constitution having a photosensitive layer 4' formed with the carrier generation layer 2 and the carrier transporting layer 3 being reversed. FIG. 3 has an intermediate layer 5 provided between the photosensitive layer 4 and the electroconductive support 1 in the layer constitution in FIG. 1, and FIG. 4 has an intermediate layer 5 provided between the photosensitive layer 4' and the electroconductive support 1 in the layer constitution in FIG. 2. The layer constitution in FIG. 5 has a photosensitive layer 4" containing a carrier generating substance 6 and a carrier transporting substance 7 formed thereon, and FIG. 6 has an intermediate layer 5 between such photosensitive layer 4" and the electroconductive support 1.

In the constitutions shown in FIG. 1 to FIG. 6, further a protective layer can be provided as the outermost layer.

In forming the photosensitive layer, the method of coating a solution containing a carrier generating substance or a carrier transporting substance alone or together with a binder or an additive dissolved therein is effective. However, on the other hand, since the solubility of a carrier generating substance is generally low, in such case, the method of coating a solution containing fine particles of a carrier generating substance dispersed in an appropriate dispersing medium by means of a dispersing device such as a ultrasonic homogenizer, ball mill, sand mill and homomixer becomes effective. In this case, the binder and the additive are generally used as added in the dispersion.

As the solvent or the dispersing medium to be used for formation of the photosensitive layer, any desired one can be widely employed. For example, there may be included butylamine, ethylenediamine, N,N-dimethylformamide, acetone, methyl ethyl ketone, cyclohexanone, tetrahydrofuran, dioxane, ethyl acetate, butyl acetate, methyl cellosolve, ethyl cellosolve, ethylene glycol dimethylether, toluene, xylene, acetophenone, chloroform, dichloromethane, dichloroethane, trichloroethane, methanol, ethanol, propanol and butanol.

When a binder is used for formation of the carrier generation layer or the carrier transporting layer, any binder can be chosen, but it should be desirably a high molecular polymer which is hydrophobic and also has film forming ability. As such polymer, the following polymers can be included, but these are not limitative of the invention:

polycarbonate, polycarbonate Z resin, acrylic resin, methacrylic resin, polyvinyl chloride, polyvinylidene chloride, polystyrene, styrene-butadiene copolymer, polyvinyl acetate, polyvinyl formal, polyvinyl butyral, polyvinyl acetal, polyvinyl carbazole, styrene-alkyd resin, silicone resin, silicone-alkyd resin, polyester, phenol resin, polyurethane, epoxy resin, vinylidene chloride-acrylonitrile copolymer, vinyl chloride-vinyl acetate copolymer, vinyl chloride-vinyl acetate-maleic anhydride copolymer.

The ratio of the carrier generating substance to the binder should be desirably 10 to 600% by weight, more preferably 50 to 400% by weight. The ratio of the carrier transporting substance to the binder should be desirably made 10 to 500% by weight. The thickness of the carrier generation layer is made 0.01 to 20 μm, but more preferably 0.05 to 5 μm. The thickness of the carrier transporting layer may be 1 to 100 μm, but more preferably 5 to 30 μm.

In the above-mentioned photosensitive layer, for the purpose of improving sensitivity, reducing residual potential or decreasing fatigue during repeated uses, an electron receiving substance can be contained. Examples of such electron receiving substance may include compounds with great electron affinity force such as succinic anhydride, maleic anhydride, dibromosuccinic anhydride, phthalic anhydride, tetrachlorophthalic anhydride, tetrabromophthalic anhydride, 3-nitrophthalic anhydride, 4-nitrophthalic anhydride, pyromellitic anhydride, mellitic anhydride, tetracyanoethylene, tetracyanoquinodimethane, o-dinitrobenzene, m-dinitrobenzene, 1,3,5-trinitrobenzene, p-nitrobenzonitrile, picryl chloride, quinonechloroimide, chloranil, bromanil, dichloro-dicyano-p-benzoquinone, anthraquinone, dinitro-anthraquinone, 9-fluorenylidene malonodinitrile, polynitro-9-fluorenylidenemalonodinitrile, picric acid, o-nitrobenzoic acid, p-nitrobenzoic acid, 3,5-dinitro-benzoic acid, pentafluorobenzoic acid, 5-nitrosalicylic acid, 3,5-dinitrosalicylic acid, phthalic acid, mellitic acid and others. The ratio of the electron receiving substance added should be desirably 0.01 to 200 wt/wt based on 100 weight of the carrier generating substance, more preferably 0.1 to 100 wt/wt.

Also, for the purpose of improving storability, durability, environmental dependency resistance, deterioration preventives such as antioxidants and photostabilizers can be contained in the above photosensitive layer. As the compound to be used for such purposes, there can be effectively used couromanol derivatives such as tocopherol, etc. and etherated compounds or esterified compounds thereof, polyarylalkane compounds, hydroquinone derivatives and mono- and di-etherated compounds thereof, benzophenone derivatives, benzotriazole derivatives, thioether compounds, phosphonic acid esters, phosphorous acid esters, phenylenediamine derivatives, phenol compounds, hindered phenol compounds, straight chain amine compounds, cyclic amine compounds, hindered amine compounds, etc. Specific examples of particularly effective compounds may include hindered phenol compounds such as "IRGANOX 1010", "IRGANOX 565" (all trade names, produced by Ciba-Geigy), "Sumilizer BHT" and "Sumilizer MDP" (all trade names, produced by Sumitomo Kagaku Kogyo), and hindered amine compounds such as "SANOL LS-2626" and "SANOL LS-622LD" (all trade names, produced by Sankyo).

As the binder to be used in intermediate layers, protective layers, etc., those mentioned above for the carrier generation layer and the carrier transporting layer can be used, but otherwise polyamide resins, ethylenic resins such as ethylene-vinyl acetate copolymer, ethylene-vinyl acetatemaleic anhydride copolymer, ethylene-vinyl acetate-methacrylic acid copolymer, etc., polyviyl alcohol, cellulose derivatives, etc. are effective. Also, curing type binders utilizing thermosetting or chemical curing such as melamine, epoxy, isocyanate, etc. can be also used.

As the electroconductive support, metal plates, metal drums can be used, or otherwise, electroconductive compounds such as electroconductive polymers, indium oxide, etc., or one having a thin layer of a metal such as aluminum, palladium, etc. provided on a substrate such as paper or plastic film by such means as coating, vapor deposition, lamination, etc. can be used.

The photoreceptor of the present invention has a constitution as described above, and is excellent in charging characteristics, sensitivity characteristics, repeating characteristics, as is also apparent from the Examples shown below.

EXAMPLES

The present invention is described below by referring to specific Examples.

Synthesis Example 1

1,3-Diiminoisoindoline (29.2 g) and sulforane (200 ml) were mixed, titanium tetraisopropoxide (17.0 g) was added, and the reaction was carried out under nitrogen atmosphere at 140° C. for 2 hours. After left to cool, the precipitates were collected by filtration, washed with chloroform, washed successively with a 2% aqueous hydrochloric acid solution, water and methanol, followed by drying to give 25.5 g (Yield: 88.8%) of titanylphthalocyanine. In the elemental analysis method, chlorine was detection limit or less.

Figure 7:
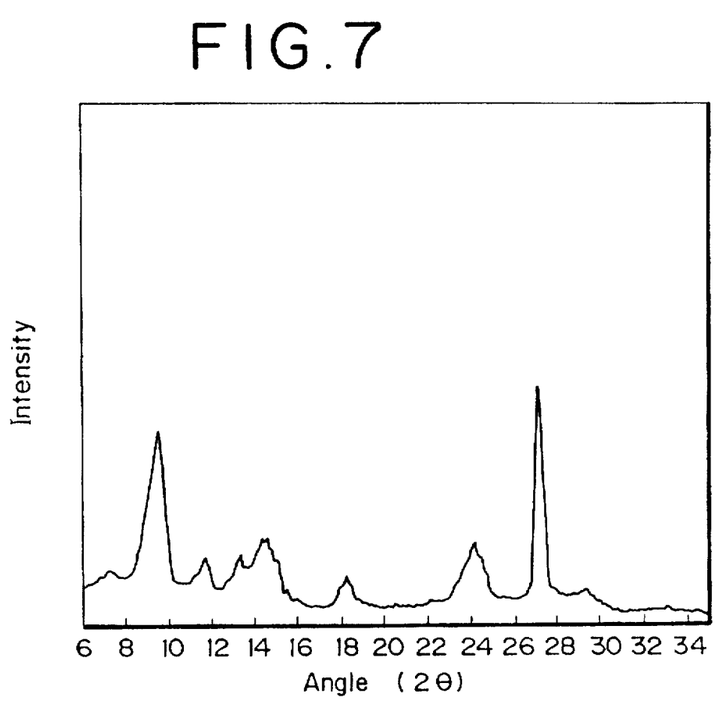
FIG. 7 and FIG. 8 are X-ray diffraction charts of the titanylphthalocyanines according to the present invention obtained in Synthesis examples 1 and 2.

The product was dissolved in 20-fold amount of conc. sulfuric acid, poured into 100-fold of water to be precipitated, and after filtration, the wet cake was treated with o-dichlorobenzene to make a crystal form having an X-ray diffraction spectrum as shown in FIG. 7.

Synthesis Example 2

1,3-Diiminoisoindoline (29.2 g) and a-chloronaphthalene (200 ml) were mixed, titanium tetrabutoxide (20.4 g) was added, and the resultant mixture was heated under nitrogen atmosphere of 140° to 150° C. for 2 hours, followed by the reaction at 180° C. for 3 hours. After left to cool, the precipitates were collected by filtration, washed successively with α-chloronaphthalene, subsequently chloroform and further a 2% aqueous hydrochloric acid solution, water and finally methanol, to give 26.2 g (91.0%) of titanylphthalocyanine after drying. The value of chlorine content in elemental analysis was 0.08% by weight.

Figure 8:
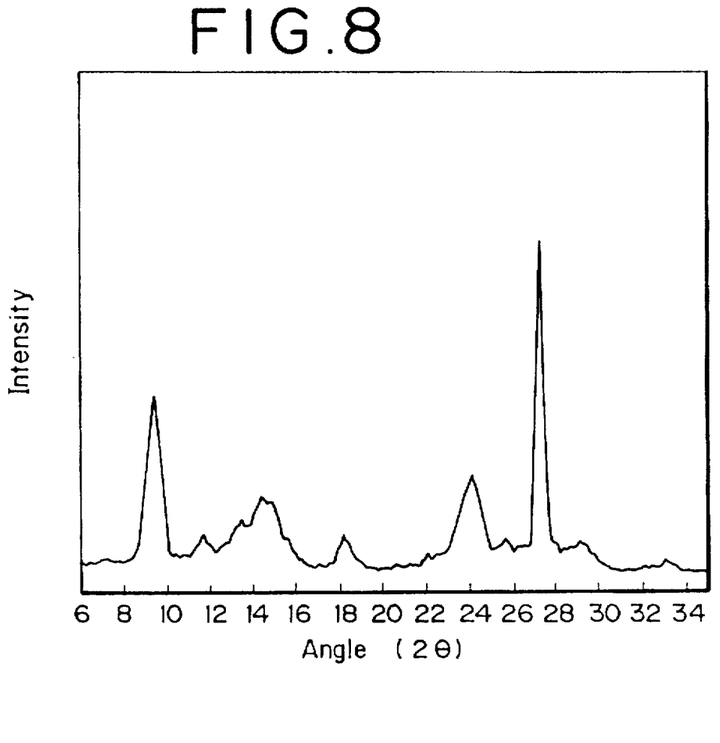

The product was dissolved in 20-fold amount of conc. sulfuric acid, poured into 100-fold of water to be precipitated, and after filtration, the wet cake was treated with 1,2-dichloroethane to make a crystal form having an X-ray diffraction spectrum as shown in FIG. 8.

Synthesis Example 3

The titanylphthalocyanine obtained in Synthesis example 1 (1.2 g) and the titanylphthalocyanine obtained in Comparative synthesis example 1 as described below (0.8 g) were dissolved in 40 g of sulfuric acid, the solution was poured into 400 g of water to effect precipitation and the precipitates were collected by filtration. The wet cake was treated with 1,2-dichloroethane to obtain a titanylphthalocyanine of the present invention with a chlorine content of 0.19% by weight.

Comparative Synthesis Example 1

Into a mixture of phthalodinitrile (25.6 g) and α-chloronaphthalene (150 ml) was added dropwise 6.5 ml of titanium tetrachloride under nitrogen atmosphere, and the reaction was carried out at a temperature of 200° to 220° C. for 5 hours. The precipitates were collected by filtration, washed with α-chloronaphthalene, then with chloroform, and subsequently with methanol. Next, the product was refluxed in ammonia water to complete hydrolysis, followed by water washing, methanol washing and drying, to give 21.8 g (75.6%) of titanylphthalocyanine. The content of chlorine by elemental analysis was 0.46% by weight.

Figure 9:
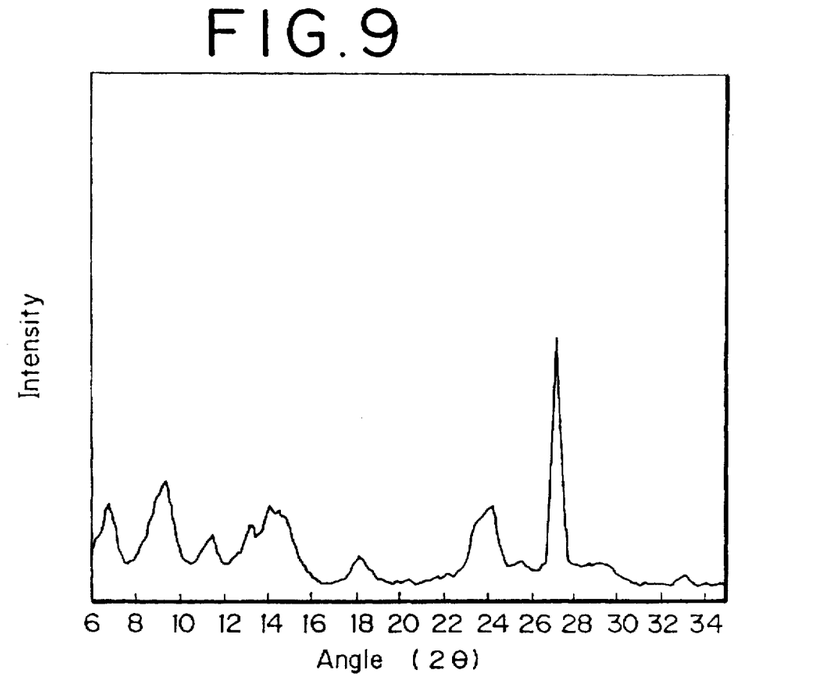
FIGS. 9 through 11 are X-ray diffraction charts of the titanylphthalocyanines obtained in Comparative synthesis examples 1, 2 and 4.

The product was dissolved in 10-fold amount of conc. sulfuric acid, poured into 100-fold of water to be precipitated, and after filtration, the wet cake was treated with 1,2-dichloroethane to make a crystal form having an X-ray diffraction spectrum as shown in FIG. 9.

Comparative Synthesis Example 2

The titanylphthalocyanine (0.6 g) obtained in Synthesis example 1 and the titanylphthalocyanine (1.4 g) obtained in Comparative example 1 were dissolved in 40 g of conc. sulfuric acid, poured into 400 g of water to effect precipitation. The precipitates were collected by filtration, and the wet cake was treated with 1,2-dichloroethane to make a crystal form having an X-ray diffraction spectrum shown in FIG. 10. The chlorine content by elemental analysis in this case was 0.31% by weight.

Comparative Synthesis Example 3

A titanylphthalocyanine for comparative purpose with a chlorine content of 1.14% by weight was obtained in the same manner as in Comparative example 1 except for using a mixture of 24.7 g of phthalodinitrile and 1.0 g of 4-chlorophthalodinitrile in place of 25.6 g of phthalodinitrile.

Comparative Synthesis Example 4

Into a mixture of phthalodinitrile (65 g) and α-chloronaphthalene (500 ml) was added dropwise 14.0 ml of titanium tetrachloride under nitrogen gas stream, and the mixture was elevated in temperature to carry out the reaction at 200° to 220° C. for 4 hours. After left to cool, the mixture was subjected to filtration at 130° C., washed with α-chloronaphthalene, followed by washing with chloroform and with methanol. Next, hydrolysis was effected in ammonia water at 70° to 80° C. for 5 hours, and the mixture was filtered, washed with water and then with methanol to give 45.2 g (yield: 62.3%) of titanylphthalocyanine. As the result of elemental analysis, the chlorine content in this product was found to be 0.42% by weight. Of the product, 8.0 g was purified by sublimation (420° C., 3×10$^4$ Torr) to obtain 2.3 g. The chlorine content after sublimation was 0.33% by weight. 2.0 Grams of the sublimated product (chlorine content 0.33% by weight) was dissolved in 20 ml of sulfuric acid, poured into 400 ml of water to be precipitated, and after filtration, the wet cake was treated with 1,2-dichloroethane to make a crystal form having an X-ray diffraction spectrum shown in FIG. 11.

Example 1

The titanylphthalocyanine having the X-ray diffraction pattern in FIG. 7 obtained in Synthesis example 1 (1 part), a silicon-modified resin, "KR-5240" (trade name, produced by Shinetsu Kagaku) as the binder resin (1.5 parts), 100 parts of isopropanol as the dispersing medium were dispersed by means of a sand mill, and the mixture was coated on a polyester base having aluminum vapor deposited thereon by means of a wire bar to form a carrier generation layer with a film thickness of 0.2 µm. Next, a solution of a carrier transporting substance T-1 (1 part), a polycarbonate resin "Yupilon Z200" (trade name, produced by Mitsubishi Gas Kagaku) (1.3 parts), and "SANOL LS-2626" (trade name, produced by Sankyo) (0.03 parts) and minute amount of silicone oil "KF-54" (trade name, produced by Shinetsu Kagaku) dissolved in 1,2-dichloroethane (10 parts) as the additives was coated by means of a blade coater and dried, to form a carrier transporting layer with a film thickness of 20 µm. The photoreceptor thus obtained is called Sample 1.

Example 2

The titanylphthalocyanine in FIG. 8 obtained in Synthesis example 2 (1 part), 1 part of a polyvinyl butyral resin "XYHL" (trade name, produced by Union Carbide) as the binder resin, 100 parts of methyl ethyl ketone as the dispersing medium were dispersed by means of a ultrasonic homogenizer. On the other hand, on a polyester base having aluminum vapor deposited thereon was provided an intermediate layer with a thickness of 0.2 µm comprising a polyamide resin "CM8000" (trade name, produced by Toray Co.), and the dispersion previously obtained was coated thereon by the dip coating method to form a carrier generation layer with a film thickness of 0.3 µm. Next, a solution of a carrier transporting substance T-2 (1 part), a polycarbonate resin "Panlite K-1300" (trade name, produced by Teijin Kasei) (1.3 parts) and a minute amount of silicone oil "KF-54" (trade name, produced by Shinetsu Kagaku) dissolved in 10 parts of 1,2-dichloroethane was coated according to the dip coating method, followed by drying, to form a carrier transporting layer with a film thickness of 22 µm.

The photoreceptor thus obtained is called Sample 2.

Example 3

A photoreceptor was prepared in the same manner as in Example 2 except for using the titanylphthalocyanine obtained in Synthesis example 3 in place of the titanylphthalocyanine in FIG. 8 in Example 2. This is called Sample 3.

Comparative Example 1

A photoreceptor for comparative purpose was obtained in the same manner as in Example 1 except for using the comparative titanylphthalocyanine having the X-ray diffraction pattern in FIG. 9 obtained in Comparative synthesis example 1 in place of the titanylphthalocyanine in FIG. 8 in Example 2. This is called Comparative sample 1.

Comparative Example 2

Figure 10:
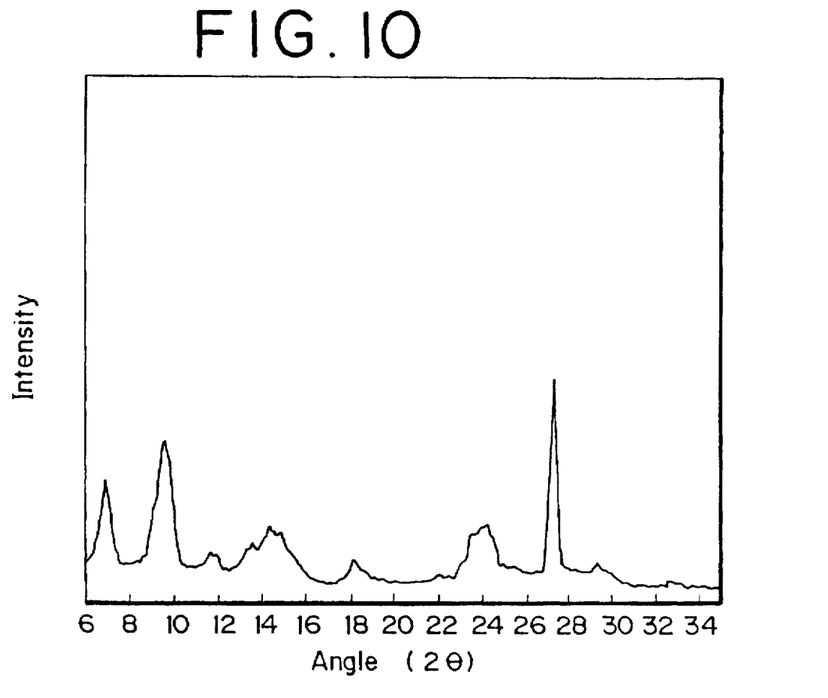

A photoreceptor for comparative purpose was obtained in the same manner as in Example 2 except for using the comparative titanylphthalocyanine having the X-ray diffraction pattern in FIG. 10 obtained in Comparative synthesis example 2 in place of the titanylphthalocyanine in FIG. 8 in Example 2. This is called Comparative sample 2.

Comparative Example 3

A photoreceptor for comparative purpose was obtained in the same manner as in Example 2 except for using the comparative titanylphthalocyanine obtained in Comparative synthesis example 3 in place of the titanylphthalocyanine in FIG. 8 in Example 2. This is called Comparative sample 3.

Comparative Example 4

Figure 11:
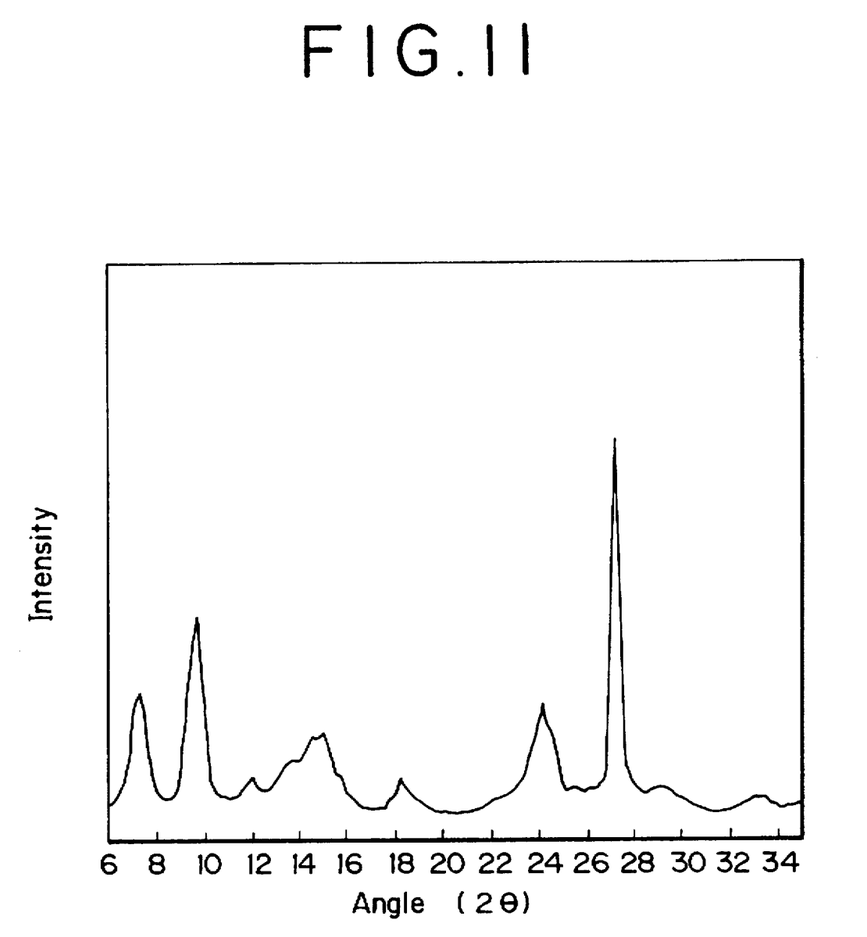

A photoreceptor was obtained in the same manner as in Example 2 except for using the titanylphthalocyanine in FIG. 11 obtained in Comparative synthesis example 4 in place of the titanylphthalocyanine in FIG. 8 in Example 2. This is called Comparative sample 4.

(Evaluation 1)

The samples obtained as described above were evaluated as described below by use of a paper analyzer EPA-8100 (trade name, produced by Kawaguchi Denki). First, corona discharging was effected for 5 seconds under the condition of −80 μA to determine the surface potential Va immediately after charging and the surface potential Vi after left to stand for 5 seconds. Subsequently, exposure to surface illuminance of 2 (lux) was effected and the dosage E1/2 necessary for making the surface potential ½ Vi was determined. Also, dark decay D was determined from the formula of D=100 (Va−Vi)/Va (%). The results are shown in Table 2. By lowering in chlorine content, characteristics particularly excellent in potential retaining ability can be obtained.

It would be clear that the samples of the present invention containing less amount of chlorine show excellent in sensitivity characteristics and remarkably small in dark decay ratio so that potential retaining ability thereof is excellent.

Particularly, when synthesized by use of a compound represented by the formula (I), dark decay percentage is small, as can be clearly seen from the photoreceptors Sample 1, Sample 2.

(Evaluation 2)

The samples obtained were also evaluated by use of a modified machine of a printer LP-3010 (trade name, produced by Konica Corp.) mounted with a semiconductor laser beam source. The potential VH at the unexposed portion, the potential VL at the exposed portion were determined, and further lowered amount ΔVH in repetition for 10,000 times were determined. The results are shown in Table 3.

TABLE 2

| Sample name | Chlorine content (%) | Va (V) | Vi (V) | D (%) | $E_{1/2}$ (lux · sec) |
|---|---|---|---|---|---|
| Sample 1 | 0 | −1350 | −1100 | 18.5 | 0.70 |
| Sample 2 | 0.08 | −1230 | −980 | 20.3 | 0.77 |
| Sample 3 | 0.19 | −1240 | −950 | 23.4 | 0.81 |
| Comparative sample 1 | 0.46 | −1090 | −790 | 27.5 | 0.90 |
| Comparative sample 2 | 0.31 | −1100 | −800 | 27.3 | 0.87 |
| Comparative sample 3 | 1.14 | −1060 | −760 | 28.3 | 0.89 |
| Comparative sample 4 | 0.33 | −1180 | −855 | 27.5 | 0.83 |

TABLE 3

| Sample name | VH (V) | VL (V) | ΔVH (V) |
|---|---|---|---|
| Sample 1 | −620 | −30 | 5 |
| Sample 2 | −600 | −30 | 10 |
| Sample 3 | −600 | −35 | 20 |
| Comparative sample 1 | −600 | −30 | 35 |
| Comparative sample 2 | −590 | −30 | 35 |
| Comparative sample 3 | −590 | −30 | 40 |
| Comparative sample 4 | −595 | −30 | 30 |

As described above, it would be clear that the samples of the present invention (Samples 1 to 3) show less lowering in potential in repeated use due to their excellent potential retaining ability.

We claim:

1. An electrophotographic photoreceptor comprising titanylphthalocyanine crystals having an X-ray diffraction spectrum to Cu—Kα line having peaks at a Bragg's angle 2θ of 27.2°±0.2°, 9.5°±0.2°, and 24.1°±0.2°,
   wherein said titanylphthalocyanine crystals have a halogen consisting of chlorine which content is not exceeding 0.2% by weight of said titanylphthalocyanine.

2. The electrophotographic photoreceptor of claim 1 wherein the titanylphthalocyanine is produced by reacting a titanium compound represented by Formula (II) with 1,3-diiminoisoindoline:

wherein $X_1$, $X_2$, $X_3$ and $X_4$ each represent, —$OR_1$, —$SR_2$, wherein $R_1$ to $R_5$ each represent a hydrogen atom, an alkyl group, an aryl group, an alkenyl group, an aryloyl group or a heterocyclic group; $X_1$ to $X_4$ may be also bonded in any combination to form a ring; Y represents a ligand, and n represents 0, 1 to 2.

3. The electrophotographic photoreceptor of claim 2 wherein the reaction is carried out at a temperature between 100° and 180° C.

4. The electrophotographic photoreceptor of claim 3 wherein the reaction is carried out at a temperature between 140° and 150° C.

5. The electrophotographic photoreceptor of claim 2 wherein the chlorine content of said titanylphthalocyanine is 0.1% or less.

6. The electrophotographic photoreceptor of claim 1 wherein the chlorine content of said titanylphthalocyanine is 0.1% or less.

7. An electrophotographic photoreceptor comprising titanylphthalocyanine crystals having an X-ray diffraction spectrum to Cu—Kα line having peaks at a Bragg's angle 2θ of 27.2°±0.2°, 9.5°±0.2°, and 24.1°±0.2°,
   wherein said titanylphthalocyanine crystals have a halogen consisting of chlorine which content does not exceed 0.2% by weight of said titanylphthalocyanine, and said titanylphthalocyanine is produced by reacting diiminoisoindoline with a titanium compound selected from the group consisting of:

(1) $(C_4H_9O)_4Ti$
(2) $(i\text{-}C_3H_7O)_4Ti$
(3) $(C_2H_5O)_4Ti$
(4) $(i\text{-}C_4H_9O)_4Ti$
(5) $(C_{18}H_{37}O)_4Ti$
(6) $(C_3H_7O)_4Ti$
(7) $(i\text{-}C_3H_7O)_2Ti(CH_3COCHCOCH_3)_2$ (8)

(9)

(10)

(11)

(12) i-C$_3$H$_7$OTi[O—P(=O)(OH)—O—P(=O)(OC$_8$C$_{17}$)$_2$]$_3$

(13) i-C$_3$H$_7$OTi(OC$_2$H$_4$NHC$_2$H$_4$NH$_2$)$_3$

(14)

(15)

(16)

(17)

(18)  and (19)

* * * * *